US012806148B2

(12) United States Patent
Masuda et al.

(10) Patent No.: US 12,806,148 B2
(45) Date of Patent: Nov. 24, 2026

(54) CANNABIDIOL-CONTAINING SEAMLESS SOFT CAPSULE

(71) Applicant: Fuji Capsule Co., LTD., Fujinomiya (JP)

(72) Inventors: Koji Masuda, Fujinomiya (JP); Takuya Kato, Fujinomiya (JP)

(73) Assignee: Fuji Capsule Co., LTD., Fujinomiya (JP)

( * ) Notice: Subject to any disclaimer, the term of this patent is extended or adjusted under 35 U.S.C. 154(b) by 565 days.

(21) Appl. No.: 18/033,005

(22) PCT Filed: Oct. 18, 2021

(86) PCT No.: PCT/JP2021/038408

§ 371 (c)(1),
(2) Date: Apr. 20, 2023

(87) PCT Pub. No.: WO2022/085622

PCT Pub. Date: Apr. 28, 2022

(65) Prior Publication Data

US 2023/0390209 A1 Dec. 7, 2023

(30) Foreign Application Priority Data

Oct. 23, 2020 (JP) ................................. 2020-177960

(51) Int. Cl.

| | |
|---|---|
| ***A61K 9/48*** | (2006.01) |
| ***A61K 9/00*** | (2006.01) |
| ***A61K 31/00*** | (2006.01) |
| ***A61K 31/427*** | (2006.01) |
| ***A61K 31/4439*** | (2006.01) |
| ***A61K 31/496*** | (2006.01) |
| ***A61K 31/546*** | (2006.01) |
| ***A61K 45/06*** | (2006.01) |
| ***A61P 1/10*** | (2006.01) |

(52) U.S. Cl.
CPC .......... *A61K 9/4825* (2013.01); *A61K 31/658* (2023.05)

(58) Field of Classification Search
CPC .. A61K 9/4825; A61K 31/658; A61K 9/0056; A61K 31/546; A61K 9/4833; A61K 9/4875; A61K 31/4439; A61K 31/496; A61K 45/06; A61K 9/4858; A61K 31/427; A61P 1/10
See application file for complete search history.

(56) References Cited

U.S. PATENT DOCUMENTS

2003/0195246 A1* 10/2003 Nakamura ........... A61K 9/4825 424/452
2006/0039959 A1 2/2006 Wessling
2006/0160888 A1* 7/2006 Kottayil .................... A61P 1/08 514/454
2009/0050163 A1 2/2009 Hartmann et al.
2015/0057342 A1* 2/2015 Koren .................. A61K 9/4875 514/456
2016/0021927 A1 1/2016 Kondo
2016/0361290 A1 12/2016 Robson et al.
2017/0172977 A1 6/2017 Kleidon et al.
2019/0247325 A1 8/2019 Kleidon
2019/0247358 A1 8/2019 Kleidon et al.
2020/0155464 A1* 5/2020 Nishimura ............. A61K 47/36
2020/0330423 A1* 10/2020 Brunn .................. A61K 9/0056
2020/0397038 A1 12/2020 Koyama
2024/0049788 A1 2/2024 Watanabe

FOREIGN PATENT DOCUMENTS

CN 106943373 A 7/2017
CN 110215443 A 9/2019
EP 0389700 A1 10/1990
EP 1361864 B1 12/2013
JP 2004-105282 A 4/2004
JP 2005-533780 A 11/2005
JP 2008-546400 A 12/2008
JP 4467883 B2 5/2010
JP 4920588 B2 4/2012
JP 2014-141433 A 8/2014
JP 2018-505912 A 3/2018
JP 2019-123681 A 7/2019
JP 2019-518760 A 7/2019
JP 2019-523775 A 8/2019
JP 6603817 B1 11/2019
JP 2022-049575 A 3/2022
WO 2002/013819 A1 2/2002
WO 2007/133140 A1 11/2007
WO 2014/171433 A1 10/2014
WO 2016/144376 A1 9/2016
WO 2019/135075 A1 7/2019
WO 2020/044123 A1 3/2020

OTHER PUBLICATIONS

International Search Report and Written Opinion for PCT/JP2021/038408, mailed Nov. 16, 2021, and English Translation of the International Search Report submitted herewith (12 pages).
Hom et al., "Soft Gelatin Capsules II: Oxygen Permeability Study of Capsule Shells", Journal of Pharmaceutical Sciences, vol. 64, No. 5, May 1975, pp. 851-857.
Health Industry Newspaper, No. 1696, Jul. 15, 2020; 5 pages.
Manabe; "Promotional Factors in Outbound Open Innovation; A Case Study on the Seamless Capsule Technology of Morishita Jintan Co., Ltd."; Journal of Intellectual Property Association of Japan; vol. 14, No. 1 (2017); 8 pages.
Office action from Japanese Patent Application No. 2022-557515 with machine translation; May 14, 2026; 8 pages.

* cited by examiner

*Primary Examiner* — Trevor Love
*Assistant Examiner* — Janet Joseph
(74) *Attorney, Agent, or Firm* — Fitch, Even, Tabin & Flannery LLP

(57) ABSTRACT

A seamless soft capsule for improving the intake efficiency of cannabidiol (CBD). The seamless soft capsule includes a capsule film, and a content enclosed in the capsule film, wherein the content contains cannabidiol.

7 Claims, No Drawings

CANNABIDIOL-CONTAINING SEAMLESS SOFT CAPSULE

CROSS-REFERENCE TO RELATED APPLICATIONS

This application is a U.S. national phase application filed under 35 U.S.C. § 371 of International Application Number PCT/JP2021/038408 filed Oct. 18, 2021, designating the United States, which claims priority from Japanese Application Number 2020-177960, filed Oct. 23, 2020.

FIELD OF THE INVENTION

The present invention relates to a cannabidiol-containing seamless soft capsule.

BACKGROUND OF THE INVENTION

*Cannabis sativa* contains various chemical substances, and these chemical substances are collectively referred to as cannabinoids. Examples of chemical substances included in cannabinoids include tetrahydrocannabinol (THC), cannabidiol (CBD), cannabichromene (CBC), cannabielsoin (CBE), cannabigerol (CBG), cannabinol (CBN), and cannabidivarin (CBDV).

The Japanese Cannabis Control Law regulates the components of *Cannabis sativa* roots, leaves, and flowers, while the components of *Cannabis sativa* seeds and mature stems are not regulated. CBD, a type of cannabinoid, is contained in *Cannabis sativa* seeds and mature stems and has been reported to have beneficial effects. For example, CBD is expected to be used for symptoms and diseases, such as stress, insomnia, schizophrenia, depression, atopic dermatitis, eating disorders (anorexia), epilepsy, drug addiction, alcoholism, obsessive-compulsive disorder, Parkinson's disease, cataract, glaucoma, Huntington's disease, amyotrophic lateral sclerosis (ALS), stroke, heart disease, liver disease, traumatic brain injury, hypertension, cellular inflammation, constipation, cancer, brain tumor, acquired immunodeficiency syndrome (AIDS), autoimmune uveitis, fibromyalgia, and osteoporosis. The World Health Organization (WHO) evaluated the safety of CBD in June 2018, and has recommended that CBD does not correspond to a narcotic under the International Narcotics Convention.

CBD-containing products have already been present. For example, there are CBD-containing foods, e-cigarettes, skin care products, refreshing oils, and bath care products. Various dosage forms containing CBD are also known (e.g., Patent Literatures 1 to 5).

CITATION LIST

Patent Literature

Patent Literature 1: Japanese Translation of PCT International Application Publication No. 2018-505912

Patent Literature 2: Japanese Translation of PCT International Application Publication No. 2019-518760

Patent Literature 3: Japanese Translation of PCT International Application Publication No. 2019-523775

Patent Literature 4: Japanese Patent No. 4467883

Patent Literature 5: Japanese Patent No. 4920588 Publication

SUMMARY OF INVENTION

An object of the present invention is to improve the intake efficiency of CBD.

As a result of intensive studies, the present inventors have found that the intake efficiency of CBD can be improved by enclosing CBD into a capsule film to form a seamless soft capsule.

The present invention includes the following embodiments.

[1]

A seamless soft capsule comprising:

a capsule film; and a content enclosed in the capsule film, wherein the content contains cannabidiol.

[2]

The seamless soft capsule according to [1], which is rapidly soluble in the oral cavity.

[3]

The seamless soft capsule according to [1], which is easily ruptured in the oral cavity.

[4]

The seamless soft capsule according to any one of [1] to [3], wherein the capsule film has a thickness of 10 to 900 μm.

[5]

The seamless soft capsule according to [4], wherein the capsule film has a thickness of 10 to 200 μm.

[6]

The seamless soft capsule according to any one of [1] to [5], wherein the seamless soft capsule has a film rate of 3 to 50%.

[7]

The seamless soft capsule according to any one of [1] to [6], wherein the seamless soft capsule has a diameter of 1 to 20 mm.

[8]

The seamless soft capsule according to any one of [1] to [7], wherein the content contains only cannabidiol as a cannabinoid.

[9]

A product comprising:

a container; and the seamless soft capsule according to any one of [1] to [8] placed in the container, wherein, as a component of the seamless soft capsule, only cannabidiol is labeled as a cannabinoid.

According to the present invention, the intake efficiency of CBD can be improved.

DESCRIPTION OF EMBODIMENTS

Embodiments of the present invention will be described in detail below; however, the present invention is not limited thereto, and can be modified in various ways within the range not deviated from the gist of the present invention.

<Seamless Soft Capsule>

An embodiment of the present invention relates to a seamless soft capsule comprising a capsule film, and a content enclosed in the capsule film (hereinafter referred to as "the capsule content"), wherein the content contains cannabidiol (CBD). Surprisingly, the seamless soft capsule according to the present embodiment can improve the stability of CBD, and thus improve the intake efficiency of CBD.

The reason for the improvement of the stability of CBD is considered as follows; however, the present invention is not limited thereby. It is assumed that CBD tends to degrade when air and light coexist. When CBD is formed into a seamless soft capsule, as can be understood from its production method (a dropping method, described later), at least air can be eliminated because there is no air inside the capsule film. It is considered that this can suppress the degradation of CBD.

[Capsule Film]

The capsule film contains a substrate (hereinafter referred to as "the capsule film substrate"). The capsule film substrate excludes water, a plasticizer, and additives from the components that constitute the capsule film. Examples of the capsule film substrate include gelatin and polysaccharides (carrageenan, gellan gum, pectin, alginates, soluble starches (starches that have been made water soluble by chemical or physical treatment), agar, etc.). Regarding soluble starches, chemical treatments include, for example, chemical modification with a hydroxypropyl group etc. Physical treatments include, for example, oxidation treatment, wet-heat treatment in the presence of salt, ultrasonic treatment, and hydrothermal treatment. The capsule film substrates may be used singly or in combination of two or more. Although it is not particularly limited, gelatin, or carrageenan and soluble starches may be used as the capsule film substrate. Gelatin derived from pig skin, cow bone, cow skin, fish scale, or the like can be used as the gelatin.

The lower limit of the amount of the capsule film substrate may be set to, for example, 20 mass %, 30 mass %, 40 mass %, 50 mass %, 60 mass %, 70 mass %, or 80 mass %, based on the total mass of all the components that constitute the capsule film (solid content excluding water). The upper limit of the amount of the capsule film substrate may be set to, for example, 100 mass %, 90 mass %, 80 mass %, 70 mass %, or 60 mass %, based on the total mass of all the components that constitute the capsule film. The lower limit and the upper limit of the amount of the capsule film substrate may be suitably combined to define a numerical range. For example, the amount of the capsule film substrate may be set to 20 to 100 mass %, 20 to 90 mass %, 20 to 80 mass %, 20 to 70 mass %, 20 to 60 mass %, 30 to 100 mass %, 30 to 90 mass %, 30 to 80 mass %, 30 to 70 mass %, 30 to 60 mass %, 40 to 100 mass %, 40 to 90 mass %, 40 to 80 mass %, 40 to 70 mass %, 40 to 60 mass %, 50 to 90 mass %, 50 to 80 mass %, 50 to 70 mass %, 50 to 60 mass %, 60 to 90 mass %, 60 to 80 mass %, 60 to 70 mass %, 70 to 90 mass %, 70 to 80 mass %, or 80 to 90 mass %, based on the total mass of all the components that constitute the capsule film.

The capsule film may further contain a plasticizer in addition to the capsule film substrate. Examples of plasticizers include polyalcohols (glycerol, polyethylene glycol, propylene glycol, polypropylene glycol, etc.), monosaccharides (glucose, fructose, glucose, galactose, etc.), disaccharides or oligosaccharides (sucrose, maltose, trehalose, coupling sugar, etc.), polysaccharides (pullulan, gum arabic, arabinogalactan, cellulose, etc.), and sugar alcohols (erythritol, xylitol, sorbitol, maltitol, lactitol, palatinit, mannitol, galactitol, etc.). The plasticizers may be used singly or in combination of two or more. Although it is not particularly limited, glycerol, sorbitol, and maltitol may be used as plasticizers.

The lower limit of the amount of the plasticizer may be set to, for example, 10 mass %, 20 mass %, 30 mass %, or 40 mass %, based on the total mass of all the components that constitute the capsule film. The upper limit of the amount of the plasticizer may be set to, for example, 60 mass %, 50 mass %, 40 mass %, 30 mass %, or 20 mass %, based on the total mass of all the components that constitute the capsule film. The lower limit and the upper limit of the amount of the plasticizer may be suitably combined to define a numerical range. For example, the amount of the plasticizer may be set to 10 to 60 mass %, 10 to 50 mass %, 10 to 40 mass %, 10 to 30 mass %, 10 to 20 mass %, 20 to 60 mass %, 20 to 50 mass %, 20 to 40 mass %, 20 to 30 mass %, 30 to 60 mass %, 30 to 50 mass-, 30 to 40 mass %, 40 to 60 mass %, or 40 to 50 mass %, based on the total mass of all the components that constitute the capsule film.

The capsule film may further contain additives. Examples of additives include coloring agents, light-shielding agents, sweeteners, flavors, preservatives, starches (without chemical or physical treatment), celluloses, pH adjusters, and neutralizers. Examples of coloring agents include natural coloring agents or synthetic coloring agents. Examples of light-shielding agents include titanium dioxide, which is a coloring agent that whitens the capsule film, and water-insoluble powder used to frost the capsule film (starches without chemical or physical treatment, celluloses, insoluble calcium, etc.).

[Capsule Content]

The capsule content contains cannabidiol (CBD) as an active ingredient. CBD may be derived from a plant or chemically synthesized. Examples of plants include hemp, cannabis, citrus, and hops.

The lower limit of the amount of CBD may be set to, for example, 1 mass %, 3 mass %, 5 mass %, 10 mass %, 20 mass %, 30 mass %, 40 mass %, 50 mass %, 60 mass %, 70 mass %, 80 mass %, or 90 mass %, based on the mass of the capsule content. The upper limit of the amount of CBD may be set to, for example, 100 mass %, 90 mass %, 80 mass %, 70 mass %, 60 mass %, 50 mass %, 40 mass %, 30 mass %, 20 mass %, 10 mass %, or 5 mass %, based on the mass of the capsule content. The lower limit and the upper limit of the amount of CBD may be suitably combined to define a numerical range. For example, the amount of CBD may be set to 1 to 100 mass %, 1 to 90 mass %, 1 to 80 mass %, 1 to 70 mass %, 1 to 60 mass %, 1 to 50 mass %, 1 to 40 mass %, 1 to 30 mass %, 1 to 20 mass %, 1 to 10 mass %, 1 to 5 mass %, 3 to 100 mass %, 3 to 90 mass %, 3 to 80 mass %, 3 to 70 mass, 3 to 60 mass %, 3 to 50 mass %, 3 to 40 mass %, 3 to 30 mass %, 3 to 20 mass %, 3 to 10 mass %, 3 to 5 mass %, 5 to 100 mass %, 5 to 90 mass %, 5 to 80 mass %, 5 to 70 mass, 5 to 60 mass %, 5 to 50 mass %, 5 to 40 mass %, 5 to 30 mass %, 5 to 20 mass %, 5 to 10 mass %, 10 to 100 mass %, 10 to 90 mass %, 10 to 80 mass %, 10 to 70 mass %, 10 to 60 mass %, 10 to 50 mass %, 10 to 40 mass %, 10 to 30 mass %, 10 to 20 mass %, 20 to 100 mass %, 20 to 90 mass %, 20 to 80 mass %, 20 to 70 mass %, 20 to 60 mass %, 20 to 50 mass %, 20 to 40 mass %, 20 to 30 mass %, 30 to 100 mass %, 30 to 90 mass %, 30 to 80 mass %, 30 to 70 mass %, 30 to 60 mass %, 30 to 50 mass %, 30 to 40 mass %, 40 to 100 mass %, 40 to 90 mass %, 40 to 80 mass %, 40 to 70 mass %, 40 to 60 mass %, 40 to 50 mass, 50 to 100 mass, 50 to 90 mass %, 50 to 80 mass %, 50 to 70 mass %, 50 to 60 mass %, 60 to 100 mass, 60 to 90 mass %, 60 to 80 mass %, 60 to 70 mass % 70 to 100 mass %, 70 to 90 mass %, 70 to 80 mass %, 80 to 100 mass %, 80 to 90 mass %, or 90 to 100 mass %, based on the mass of the capsule content.

The form of the capsule content is, for example, a solution, dispersion, or paste. The capsule content in the form of a solution can be prepared by dissolving CBD in a liquid that can dissolve CBD. The capsule content in the form of a dispersion can be prepared by dispersing CBD with an emulsifier in a liquid that does not dissolve or hardly dissolves CBD. The capsule content in the form of a paste can be prepared by heating and dissolving a thickener, a hardened oil, and a wax in appropriate liquid fats and oils, followed by stirring, cooling, and defoaming, thereby obtaining a paste base, and then adding CBD thereto to homogenize the paste.

The capsule content may further contain an active ingredient (hereinafter referred to as "the second active ingredient") in addition to CBD. In the present specification, the term "active ingredient" refers to an ingredient that exerts effects, functions, usefulness, etc. that are indicated, advertised, and suggested regarding products containing seamless soft capsules. The second active ingredients may be used singly or in combination of two or more. Examples of the second active ingredient include cannabinoids other than CBD. Examples of such cannabinoids include tetrahydrocannabinol (THC), cannabichromene (CBC), cannabielsoin (CBE), cannabigerol (CBG), cannabinol (CBN), and cannabidivarin (CBDV). As an example, the capsule content may contain CBD and THC.

The capsule content may contain only CBD and cannabinoids other than CBD as active ingredients.

The capsule content may contain only CBD as an active ingredient.

The capsule content may contain CBD as an active ingredient and may not contain cannabinoids other than CBD.

The capsule content may contain CBD as an active ingredient and may not contain THC.

The capsule content may contain CBD as an active ingredient and may not contain terpene.

The capsule content may contain only CBD as a cannabinoid.

The capsule content may not contain THC.

The capsule content may not contain terpene.

Whether or not to contain "only CBD as a cannabinoid" is based on the time of production of the seamless soft capsule. That is, for example, even if cannabinoids other than CBD are generated over time, when the seamless soft capsule contains only CBD as a cannabinoid at the time of production, it is supposed to contain "only CBD as a cannabinoid."

When the capsule content contains a second active ingredient, the lower limit of the amount of CBD may be set to, for example, 1 mass %, 5 mass %, 10 mass %, 20 mass %, 30 mass %, 40 mass %, 50 mass %, 60 mass %, 70 mass %, or 80 mass %, based on the total mass of all the active ingredients. The upper limit of the amount of CBD may be set to, for example, 95 mass %, 90 mass %, 80 mass %, 70 mass %, or 60 mass %, based on the total mass of all the active ingredients. The lower limit and the upper limit of the amount of CBD may be suitably combined to define a numerical range. For example, the amount of CBD may be set to 1 to 95 mass %, 1 to 90 mass %, 1 to 80 mass %, 1 to 70 mass %, 1 to 60 mass %, 5 to 95 mass %, 5 to 90 mass, 5 to 80 mass %, 5 to 70 mass %, 5 to 60 mass %, 10 to 95 mass %, 10 to 90 mass %, 10 to 80 mass %, 10 to 70 mass %, 10 to 60 mass %, 20 to 95 mass %, 20 to 90 mass %, 20 to 80 mass %, 20 to 70 mass %, 20 to 60 mass %, 30 to 95 mass %, 30 to 90 mass %, 30 to 80 mass %, 30 to 70 mass %, 30 to 60 mass %, 40 to 95 mass %, 40 to 90 mass %, 40 to 80 mass %, 40 to 70 mass %, 40 to 60 mass %, 50 to 95 mass %, 50 to 90 mass %, 50 to 80 mass %, 50 to 70 mass %, 50 to 60 mass %, 60 to 95 mass %, 60 to 90 mass %, 60 to 80 mass %, 60 to 70 mass %, 70 to 95 mass %, 70 to 90 mass %, 70 to 80 mass %, 80 to 95 mass %, or 80 to 90 mass %, based on the total mass of all the active ingredients.

The capsule content may further contain other components in addition to the active ingredients. Examples of such components include fats and oils, waxes, hardened oils, mineral oils, fatty acids, stimulants, sweeteners, and flavors.

Examples of fats and oils include avocado oil, almond oil, linseed oil, fennel oil, perilla oil, olive oil, olive squalene, orange oil, orange rough oil, sesame oil, garlic oil, cacao butter, pumpkin seed oil, chamomile oil, carrot oil, cucumber oil, beef tallow fatty acid, kukui nut oil, cranberry seed oil, brown rice germ oil, rice oil, wheat germ oil, safflower oil, shea butter, liquid shea butter, shiso-herb oil, soybean oil, evening primrose oil, camellia oil, corn oil, rapeseed oil, saw palmetto extract oil, coix seed oil (INCI name: oix Lacryma-Jobi Ma-yuen Seed Oil), persic oil, parsley seed oil, castor oil, sunflower oil, grape seed oil, borage oil, macadamia nut oil, meadowfoam oil, cottonseed oil, peanut oil, turtle oil, mink oil, egg yolk oil, fish oil, palm oil, palm kernel oil, Japan wax, coconut oil, long-, medium-, or short-chain fatty acid triglycerides, diacylglycerides, beef tallow, pork fat, squalene, squalane, pristane, and hydrogen additives of these fats and oils.

Examples of waxes include shellac wax, beeswax, carnauba wax, whale wax, lanolin, liquid lanolin, reduced lanolin, hard lanolin, cyclic lanolin, lanolin wax, candelilla wax, Japan wax, montan wax, and rice wax.

Examples of hardened oils include plant hardened oil (hydrogen additives of plant fats and oils), beef tallow hardened oil, and pork fat hardened oil.

Examples of mineral oils include liquid paraffin, vaseline, paraffin, ozokerite, ceresin, and microcrystalline wax.

Examples of fatty acids include natural fatty acids (lauric acid, myristic acid, palmitic acid, stearic acid, behenic acid, oleic acid, linoleic acid, conjugated linoleic acid, linolenic acid, docosahexaenoic acid, eicosapentaenoic acid, 12-hydroxystearic acid, undecylenic acid, tall oil, lanolin fatty acid, etc.), and synthetic fatty acids (isononanoic acid, caproic acid, 2-ethylbutanoic acid, isopentanoic acid, 2-methylpentanoic acid, 2-ethylhexanoic acid, isopentanoic acid, etc.).

Examples of stimulants include capsicum tincture, capsicum oil, nonanoic acid vanillylamide, cantharides tincture, ginger tincture, ginger oil, mentha oil, 1-menthol, camphor, and benzyl nicotinate.

Examples of sweeteners include sucrose, stevia, glycyrrhizin, *Siraitia grosvenorii*, somatin, saccharin, aspartame, acesulfame potassium, sucralose, erythritol, xylitol, sorbitol, palatinit, maltitol, lactitol, and mannitol.

Examples of flavors include fruit-based flavors (lemon flavor, orange flavor, grape flavor, etc.), mint flavors, and menthol flavors.

The capsule content may contain an emulsifier for the purpose of maintaining the homogeneity of each component and improving absorption in the body, but may not contain an emulsifier.

The capsule content may contain a self-emulsifier for the purpose of improving absorption in the body, but may not contain a self-emulsifier.

The capsule content may contain glyceryl monooleate and/or glyceryl monostearate for the purpose of maintaining the homogeneity of each component and improving absorption in the body, but may not contain glyceryl monooleate and/or glyceryl monostearate.

[Seamless Soft Capsule]

The lower limit of the diameter of the spherical seamless soft capsule may be set to, for example, 1 mm, 3 mm, 5 mm, or 10 mm. The upper limit of the diameter of the seamless soft capsule may be set to, for example, 20 mm, 15 mm, 10 mm, or 5 mm. The lower limit and the upper limit of the diameter of the seamless soft capsule may be suitably combined to define a numerical range. For example, the diameter of the seamless soft capsule may be set to 1 to 20 mm, 1 to 15 mm, 1 to 10 mm, 1 to 5 mm, 3 to 20 mm, 3 to 15 mm, 3 to 10 mm, 3 to 5 mm, 5 to 20 mm, 5 to 15 mm, 5 to 10 mm, 10 to 20 mm, or 10 to 15 mm.

The seamless soft capsule may have a frosted surface or a glossy surface. The frosted surface can be formed, for example, by adding water-insoluble powder (starches without chemical or physical treatment, celluloses, water-soluble calcium, etc.) as a component of the capsule film, or adding in excess crystalline powder, such as erythritol, as a component of the capsule film, and drying the capsule film to precipitate crystals.

The capsule film of the seamless soft capsule may be transparent or colored. When the capsule film is colored, the color may be, for example, brown. The colored capsule film can be formed, for example, by adding a coloring agent and a light-shielding agent as components of the capsule film.

The lower limit of the thickness of the capsule film of the seamless soft capsule may be set to, for example, 10 μm, 20 μm, 50 μm, 100 μm, or 200 μm. The upper limit of the thickness of the capsule film may be set to, for example, 900 μm, 600 μm, 400 μm, 200 μm, 170 μm, or 130 m. The lower limit and the upper limit of the thickness of the capsule film may be suitably combined to define a numerical range. For example, the thickness of the capsule film may be set to 10 to 900 μm, 10 to 600 μm, 10 to 400 μm, 10 to 200 μm, 10 to 170 μm, 10 to 130 μm, 20 to 900 μm, 20 to 600 μm, 20 to 400 μm, 20 to 200 μm, 20 to 170 μm, 20 to 130 μm, 50 to 900 μm, 50 to 600 μm, 50 to 400 μm, 50 to 200 μm, 50 to 170 μm, 50 to 130 μm, 100 to 900 μm, 100 to 600 μm, 100 to 400 μm, 100 to 200 μm, 100 to 170 μm, 100 to 130 μm, 200 to 900 μm, 200 to 600 μm, or 200 to 400 μm. When the thickness of the capsule film varies depending on the site of the seamless soft capsule, the thickness is measured at the site of maximum thickness of the capsule film. The method for measuring the thickness of the capsule film is as described in the Examples.

The lower limit of the film rate of the seamless soft capsule may be set to, for example, 3%, 4%, 8%, 12%, or 16%. The upper limit of the film rate may be set to, for example, 50%, 40%, 30%, 20%, 18%, 16%, 14%, or 12%. The lower limit and the upper limit of the film rate may be suitably combined to define a numerical range. For example, the film rate may be set to 3 to 50%, 3 to 40%, 3 to 30%, 3 to 20%, 3 to 18%, 3 to 16%, 3 to 14%, 3 to 12%, 4 to 50%, 4 to 40%, 4 to 30%, 4 to 20%, 4 to 18%, 4 to 16%, 4 to 14%, 4 to 12%, 8 to 50%, 8 to 40%, 8 to 30%, 8 to 20%, 8 to 18%, 8 to 16%, 8 to 143, 8 to 12%, 12 to 50%, 12 to 40%, 12 to 30%, 12 to 20%, 12 to 18%, 12 to 16%, 12 to 14%, 16 to 50%, 16 to 40%, 16 to 30%, 16 to 20%, or 16 to 18%. In the present specification, the "film rate" refers to the ratio of the mass of the capsule film to the mass of the seamless soft capsule. The method for measuring the film rate is as described in the Examples.

The inner space of the seamless soft capsule formed by the capsule film of the seamless soft capsule is preferably completely filled with the capsule content. In the present specification, the phrase "completely filled" means that the capsule content is inserted so that there is no gap (no gas exists) between the inner surface of the capsule film and the capsule content.

When the seamless soft capsule is exposed to light with a total illuminance of 1.2 million lux·hr, the residual rate of CBD is preferably 80% or more, more preferably 90% or more, even more preferably 95% or more, and particularly preferably 98% or more. The conditions of light irradiation are as described in the Examples.

The seamless soft capsule may be configured to be suitable for sublingual administration. Sublingual administration improves the intake efficiency of CBD because of its superior bioavailability.

The seamless soft capsule may be rapidly soluble in the oral cavity. In the present specification, the phrase "rapidly soluble in the oral cavity" means that the disintegration time measured by an oral disintegration tester is 60 seconds or less. Specifically, using the Tricorp Tester (produced by Okada Seiko Co., Ltd.), the seamless soft capsule is sandwiched between upper and lower metal meshes, artificial saliva is dropped while applying a load to the upper mesh, and the time when the seamless soft capsule is disintegrated so that the upper and lower meshes come into contact with each other is defined as the disintegration time. The measurement conditions are as described below.

Load: 40 g

Artificial saliva (KCl: 1.47 g/L, NaCl: 1.44 g/L, Tween 80: 0.3%)

Liquid temperature: 37° C.

Drop rate: 6 mL/min

The seamless soft capsule may be easily ruptured in the oral cavity. In the present specification, the phrase "easily ruptured in the oral cavity" means that the content can be easily released by chewing in the oral cavity.

Examples of routes of administration of the seamless soft capsule include sublingual administration and oral administration. Although it is not particularly limited, sublingual administration is preferred.

The seamless soft capsule can be used, for example, as a medicament, quasi-drug, or food. Examples of foods include general foods and foods with health claims (foods for specified health uses, foods with function claims, foods with nutrient function claims, etc.).

Examples of symptoms and diseases treated with the seamless soft capsule include stress, insomnia, schizophrenia, depression, atopic dermatitis, eating disorders (anorexia), epilepsy, drug addiction, alcoholism, obsessive-compulsive disorder, Parkinson's disease, cataract, glaucoma, Huntington's disease, amyotrophic lateral sclerosis (ALS), stroke, heart disease, liver disease, traumatic brain injury, hypertension, cellular inflammation, constipation, cancer, brain tumor, acquired immunodeficiency syndrome (AIDS), autoimmune uveitis, fibromyalgia, and osteoporosis.

(Seamless Soft Capsule A)

An embodiment of the seamless soft capsule is a seamless soft capsule comprising a capsule film comprising carrageenan, an acidic pH adjuster, and a neutralizer (hereinafter referred to as "the capsule film A") (hereinafter referred to as "the seamless soft capsule A"). Because these components are contained, it is possible to obtain a fragile capsule film while maintaining its hardness. Making the capsule film fragile is advantageous, for example, in facilitating sublingual administration.

The capsule film A can be produced through the process of degrading carrageenan with an acidic pH adjuster and stopping the degradation with a neutralizer. By adjusting the degree of degradation, an appropriate viscosity can be obtained. The viscosity may be adjusted to, for example, 30 to 150 mPa-s or 50 to 100 mPa-s. The viscosity can be measured by using a "C-type viscometer CVR-20 produced by Tokimec Co., Ltd." at a liquid temperature of 75° C.

When the viscosity is 100 mPa-s or less, Rotor No. 0 can be used, and when the viscosity exceeds 100 mPa-s, Rotor No. 1 can be used.

Examples of carrageenan in the capsule film A include κ-carrageenan, ι-carrageenan, and λ-carrageenan. Although it is not particularly limited, κ-carrageenan is preferably used.

The amount of carrageenan in the capsule film A may be set to, for example, 50% or more, or 70% or more, based on the total mass of all the components that constitute the capsule film.

Examples of the acidic pH adjuster in the capsule film A include citric acid, malic acid, acetic acid, formic acid, oxalic acid, lactic acid, phytic acid, and hydrochloric acid.

Examples of the neutralizer in the capsule film A include alkalis, such as disodium hydrogen phosphate, sodium citrate, and sodium hydrogen carbonate.

The diameter of the seamless soft capsule A may be set to, for example, 0.5 to 15 mm or 1 to 8 mm.

The thickness of the capsule film A may be set to, for example, 40 μm or less, or 30 μm or less.

The film rate of the capsule film A may be set to, for example, 5 to 20% or 7 to 15'.

The capsule film A may further contain, for example, plasticizers, alginates, sugars, dextrins, starches, or modified starches.

(Seamless Soft Capsule B)

An embodiment of the seamless soft capsule is a seamless soft capsule comprising a capsule film comprising sorbitol, maltitol, and glycerol as plasticizers (hereinafter referred to as "the capsule film B") (hereinafter referred to as "the seamless soft capsule B"). A capsule film having excellent flexibility can be obtained by containing these components in predetermined amounts.

When the main component of the capsule film substrate is gelatin, the amount of sorbitol is preferably 1 to 15 parts by mass, the amount of maltitol is preferably 1 to 30 parts by mass, and the amount of glycerol is preferably 40 to 60 parts by mass, based on 100 parts by mass of gelatin.

When the main component of the capsule film substrate is a mixture of starch and carrageenan, the amount of sorbitol is preferably 1 to 15 parts by mass, the amount of maltitol is preferably 1 to 30 parts by mass, and the amount of glycerol is preferably 30 to 60 parts by mass, based on 100 parts by mass of the mixture.

Examples of carrageenan in the capsule film A include κ-carrageenan and ι-carrageenan.

Examples of starch in the capsule film A include oxidized starch, starch dispersion, wet heat-treated starch, and acid-treated starch.

<Product>

An embodiment of the present invention relates to a product comprising a container, and the seamless soft capsule placed in the container. The shape, material, etc. of the container are not particularly limited, and any container that can accommodate seamless soft capsules may be used.

Only CBD and cannabinoids other than CBD as active ingredients may be labeled on the product as components of the seamless soft capsule.

Only CBD as an active ingredient may be labeled on the product as a component of the seamless soft capsule.

CBD as an active ingredient may be labeled on the product as a component of the seamless soft capsule, and cannabinoids other than CBD may not be labeled.

CBD as an active ingredient may be labeled on the product as a component of the seamless soft capsule, and THC may not be labeled.

CBD as an active ingredient may be labeled on the product as a component of the seamless soft capsule, and terpene may not be labeled.

Only CBD may be labeled as a cannabinoid on the product as a component of the seamless soft capsule.

THC may not be labeled on the product as a component of the seamless soft capsule.

Terpene may not be labeled on the product as a component of the seamless soft capsule.

Examples of labeling on the product include labeling on the container, instructions, or packaging.

<Method for Producing Seamless Soft Capsule>

The method for producing the seamless soft capsule is not particularly limited, and a known method can be used. Examples of the method for producing the seamless soft capsule include a dropping method (including an in-liquid dropping method in which double droplets are ejected while the concentric double nozzle is immersed in a carrier liquid, and an in-air dropping method in which the concentric double nozzle is suspended from a carrier liquid and droplets are ejected in the air).

In the dropping method, the size of the seamless soft capsule can be adjusted, for example, by changing the size of the nozzles that drop the capsule film liquid and the capsule content.

In the dropping method, the thickness of the capsule film and the film rate can be adjusted, for example, by changing the size of the nozzle through which the capsule film liquid passes.

EXAMPLES

The present invention will be described in more detail below using Examples and a Comparative Example; however, the technical scope of the present invention is not limited thereto.

<Measurement Method>

[Film Thickness]

The thickness of the capsule film was measured by using a high-resolution 3D X-ray microscope "nano3DX" (produced by Rigaku Corporation). This microscope can observe the cross-sectional state non-destructively, and the difference in density is imaged as contrast. A molybdenum target was used as the X-ray source, the lens magnification was 1.25×, the pixel size was 0.7 μm/voxel, the exposure time was 8 seconds, and the number of cross-sections was 400. The center (equatorial plane) of the capsule was analyzed and imaged, the film thickness of each capsule was measured at 4 points on the top, bottom, left, and right, and the average value was defined as the film thickness of the capsule. The average of 3 capsules was taken.

[Film Rate]

The ratio of the mass of the capsule film to the total mass of the capsule was defined as the film rate. Each mass was measured using an ordinary electronic balance.

[Size of Seamless Soft Capsule]

The diameter of the seamless soft capsule was measured using a caliper.

Production Example 1

[Production of Seamless Soft Capsule]

(1) Preparation of Capsule Film Liquid

Gelatin (10 kg), glycerol (5.0 kg), erythritol (2.0 kg), xylit (0.5 kg), and water (50.0 kg) were mixed, and the mixture was stirred while heating until gelatin was dissolved, followed by filtration through a 100-mesh sieve, thereby preparing a capsule film liquid.

(2) Preparation of Capsule Content

10% CBD oil (2.5 kg) consisting of CBD (10%) and organic hemp oil (90), rapeseed salad oil (2.25 kg), and 1-menthol (0.25 kg) were mixed, and the mixture was stirred until 1-menthol was dissolved, followed by filtration through a 100-mesh sieve, thereby preparing a capsule content.

(3) Production of Seamless Soft Capsule

The capsule film liquid and the capsule content were used to form a seamless soft capsule by a dropping method. Specifically, the capsule film liquid was dropped from the outer nozzle of a concentric double nozzle, and the capsule content was dropped from the inner nozzle into cooled MCT oil (medium-chain fatty acid triglyceride) to form a capsule with a capacity of 200 mg in which the inner space of the capsule was completely filled with the content. Next, the MCT oil attached to the obtained capsule was removed, followed by drying and washing with ethanol, thereby producing a spherical seamless soft capsule having an almost colorless capsule film with a frosted surface. The film rate of the seamless soft capsule was 12%, the film thickness was 112 μm, and the size was 7.1 mm.

Production Example 2

A spherical seamless soft capsule having an almost colorless and transparent capsule film with a glossy surface was produced in the same manner as in Production Example 1, except that the formulation of the capsule film liquid in Production Example 1 was changed to an erythritol-free formulation. The film rate of the seamless soft capsule was 12%, the film thickness was 123 μm, and the size was 7.0 mm.

Production Example 3

A spherical seamless soft capsule having an almost colorless and transparent capsule film with a glossy surface was produced in the same manner as in Production Example 2, except that the proportion of the capsule film liquid and the capsule content in Production Example 2 was changed. The film rate of the seamless soft capsule was 8%, the film thickness was 100 μm, and the size was 6.7 mm.

Production Example 4

A spherical seamless soft capsule having a brown transparent capsule film with a glossy surface was produced in the same manner as in Production Example 2, except that a caramel coloring agent (0.5 kg) was added to the capsule film liquid in Production Example 2. The film rate of the seamless soft capsule was 12%, the film thickness was 120 μm, and the size was 7.0 mm.

<Stability Test>

The stability of the seamless soft capsules produced in Production Examples 1 to 4 was evaluated. The capsule content of Production Example 1 (without a capsule film) was used as the Comparative Example. As shown in the following Table 1, the residual rate of CDB when stored under predetermined conditions in each storage container was measured by liquid chromatography.

The following devices were used in this test.

Fluorescent lamp: FL20SS/EX-D/18M (produced by Panasonic Holdings Corporation)

Digital illuminometer: LX-1000 (produced by Custom Corporation)

Temperature-humidity data logger memory meter: SK-L200TH IIα (produced by Sato Keiryoki Mfg. Co., Ltd.)

The conditions of liquid chromatography are as follows.

Detector: photodiode array (measurement wavelength: 220 nm)

Column: Chemco Pak CHEMCOSORB 5-ODS-H

Colum temperature: 30° C.

Sample cooler temperature: 5° C.

Injection volume: 10 μL

Flow rate: 1.0 mL/min

Mobile phase A: water/acetic acid (1000/1)

Mobile phase B: acetonitrile/acetic acid (1000/1)

(From 0 to 20 minutes after injection, the mixing ratio of the mobile phases A and B was changed from 50 to 30 vol % for the mobile phase A and from 50 to 70 vol % for the mobile phase B.)

Table 1 shows the results of the stability test.

TABLE 1

| | Storage container | Storage conditions | | CBD residual rate |
|---|---|---|---|---|
| Comparative Example | Brown vial bottle (sealed) | Initial | Room temperature | 100.0% |
| | Petri dish (open) | 2000 lux/day: 14 days | 30.3° C., 39.2RH | 83.5% |
| | | 2000 lux/day: 25 days | (average value) | 67.1% |
| Production Example 1 | Aluminum zip (sealed) | Initial | Room temperature | 100.0% |
| | Petri dish (open) | 2000 lux/day: 14 days | 30.3° C., 39.2RH | 97.6% |
| | | 2000 lux/day: 25 days | (average value) | 96.3% |
| Production Example 2 | Aluminum zip (sealed) | Initial | Room temperature | 100.0% |
| | Petri dish (open) | 2000 lux/day: 14 days | 30.3° C., 39.2RH | 100.0% |
| | | 2000 lux/day: 25 days | (average value) | 98.7% |
| Production Example 3 | Aluminum zip (sealed) | Initial | Room temperature | 100.0% |
| | Petri dish (open) | 2000 lux/day: 14 days | 30.3° C., 39.2RH | 101.3% |
| | | 2000 lux/day: 25 days | (average value) | 98.7% |
| Production Example 4 | Aluminum zip (sealed) | Initial | Room temperature | 100.0% |
| | Petri dish (open) | 2000 lux/day: 14 days | 30.3° C., 39.2RH | 101.3% |
| | | 2000 lux/day: 25 days | (average value) | 101.3% |

The light stability test in medicament approval applications requires stability when exposed to light with a total illuminance of 1.2 million lux-hr. The total illuminance of 1.2 million lux-hr corresponds to the 25-day exposure at 2000 lux in Table 1. As shown in Table 1, in the Comparative Example, which did not have a capsule film, the residual rate of CBD decreased significantly with the lengthening of the storage period under light irradiation, whereas in the seamless soft capsules of Production Examples 1 to 4, no significant decrease was observed in the residual rate of CBD, confirming that they had excellent stability.

The invention claimed is:

1. A seamless soft capsule comprising: a capsule film; and a content enclosed in the capsule film, wherein the content contains cannabidiol in an amount of 3 mass % or more based on the mass of the capsule content and the capsule content does not include a self-emulsifier and the capsule film comprises a gelatin as a main component, and wherein the capsule film has a thickness of 10 to 200 μm.

2. The seamless soft capsule according to claim 1, which is rapidly soluble in the oral cavity.

3. The seamless soft capsule according to claim 1, which is easily ruptured in the oral cavity.

4. The seamless soft capsule according to claim 1, wherein the seamless soft capsule has a film rate of 3 to 50%.

5. The seamless soft capsule according to claim 1, wherein the seamless soft capsule has a diameter of 1 to 20 mm.

6. The seamless soft capsule according to claim 1, wherein the content contains only cannabidiol as a cannabinoid.

7. A product comprising:

a container; and the seamless soft capsule according to claim 1 placed in the container, wherein, as a component of the seamless soft capsule, only cannabidiol is labeled as a cannabinoid.

* * * * *